(12) United States Patent
Bernard et al.

(10) Patent No.: US 9,290,553 B2
(45) Date of Patent: Mar. 22, 2016

(54) PEPTIDES THAT MODULATE COMPLEX SASPASE-FLG2

(75) Inventors: Dominique Bernard, Vanves (FR); Agnes Thomas-Collignon, Montigny le Bretonneux (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/992,564

(22) PCT Filed: Dec. 5, 2011

(86) PCT No.: PCT/IB2011/055461
§ 371 (c)(1),
(2), (4) Date: Aug. 9, 2013

(87) PCT Pub. No.: WO2012/077037
PCT Pub. Date: Jun. 14, 2012

(65) Prior Publication Data
US 2013/0324477 A1    Dec. 5, 2013

Related U.S. Application Data

(60) Provisional application No. 61/457,090, filed on Dec. 23, 2010.

(30) Foreign Application Priority Data

Dec. 7, 2010 (FR) .................................. 10 60177

(51) Int. Cl.
| | | |
|---|---|---|
| *A61K 8/64* | (2006.01) | |
| *C07K 14/47* | (2006.01) | |
| *A61Q 19/00* | (2006.01) | |
| *C12N 9/64* | (2006.01) | |
| *G01N 33/573* | (2006.01) | |
| *A61K 8/60* | (2006.01) | |
| *G01N 33/68* | (2006.01) | |

(52) U.S. Cl.
CPC ............... *C07K 14/47* (2013.01); *A61K 8/606* (2013.01); *A61K 8/64* (2013.01); *A61Q 19/00* (2013.01); *C07K 14/4713* (2013.01); *C12N 9/6413* (2013.01); *G01N 33/573* (2013.01); *G01N 33/6881* (2013.01); *A61K 2800/10* (2013.01); *C07K 2319/02* (2013.01); *C07K 2319/10* (2013.01); *C07K 2319/21* (2013.01); *C07K 2319/23* (2013.01); *C07K 2319/24* (2013.01); *C07K 2319/60* (2013.01); *G01N 2333/96472* (2013.01); *G01N 2500/02* (2013.01)

(58) Field of Classification Search
CPC ..... A61K 8/64; A61K 2800/10; A61Q 19/00; C07K 14/47; C07K 2319/02; C07K 2319/10; C07K 2319/21; C07K 2319/23; C07K 2319/24; C07K 2319/60
USPC ......................................... 514/18.8; 530/321
See application file for complete search history.

(56) References Cited

U.S. PATENT DOCUMENTS

| 7,521,422 B2 | 4/2009 | Bernard et al. |
|---|---|---|
| 2004/0053248 A1* | 3/2004 | Tang et al. .................. 435/6 |
| 2004/0142331 A1* | 7/2004 | Jackson et al. ............. 435/6 |
| 2009/0186821 A1 | 7/2009 | Bernard et al. |
| 2010/0005534 A1 | 1/2010 | Matsui et al. |

FOREIGN PATENT DOCUMENTS

| EP | 1 935 243 | 6/2008 |
|---|---|---|
| FR | 2 842 209 | 1/2004 |

OTHER PUBLICATIONS

Effects of Aging on the Skin from Merck Manual, p. 1. Accessed Apr. 9, 2012.*
Chronic effects of sunlight from Merck Manual, pp. 1-2. Accessed Aug. 23, 2012.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of Escherichia coli maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
water definition from www.biology-online.org/dictionary/Water, pp. 1-3. Accessed Apr. 24, 2014.*
Q5D862 from NCBI, pp. 1-7. Accessed Mar. 9, 2015.*
Toulza, E. et al., "Large-scale identification of human genes implicated in epidermal barrier function", Genome Biology, vol. 8, No. 6, Total pp. 23, (Jun. 11, 2007), XP021031239.
Wu, Zhihong et al., "Molecular Identification and Expression Analysis of Filagfrin-2, a Member of the S100 Fused-Type Protein Family", PlosONE, vol. 4, No. 4, pp. 1 to 13, (Apr. 2009), XP009150055.
International Search Report Issued Jul. 16, 2012 in PCT/IB11/55461 Filed Dec. 5, 2011.
French Search Report Issued Jul. 7, 2011 in French Patent Application 1060177 Filed Dec. 7, 2010.
Written Opinion of the International Searching Authority Issued Jul. 16, 2012 in PCT/IB 2011/055461 Filed Dec. 5, 2011.
U.S. Appl. No. 13/992,589, filed Jun. 7, 2013, Bernard, et al.

* cited by examiner

*Primary Examiner* — Julie Ha
(74) *Attorney, Agent, or Firm* — Oblon, McClelland, Maier & Neustadt, L.L.P.

(57) ABSTRACT

An isolated peptide from skin aspartic protease (SASPase) or filaggrin-2 (FLG2), a fragment or homologue thereof, which can modify the three-dimensional shape of a complex formed by interaction between a first amino acid sequence from filaggrin-2 and a second amino acid sequence from SASPase, is described. The isolated peptide is useful as a target for screening for cosmetic or therapeutic active agents with regard to the skin and/or its appendages.

3 Claims, No Drawings

PEPTIDES THAT MODULATE COMPLEX SASPASE-FLG2

The present invention relates to a novel cosmetic or therapeutic target with regard to the skin and/or its appendages, and also to the use thereof for the purposes of a biological marker of the skin or for screening for new active agents dedicated to the cosmetic, therapeutic or dermatological care of the skin and/or its appendages.

More specifically, the present invention relates to isolated peptides, which are respectively from filaggrin-2 (FLG2), and from skin aspartic protease (SASPase), capable of together forming a complex, and to the use thereof as a target for screening for cosmetic or therapeutic active agents with regard to the skin and/or its appendages.

The expression "the skin and its appendages" means the whole of the skin of the body, the scalp, the mucous membranes, and in particular the lips, body hair, the hair and the nails. More particularly, the present invention relates to the skin of the body, the scalp, the lips, the hair and body hair. In particular, the present invention relates to the skin of the face, of the neckline, of the arms and forearms, and of the legs, and the scalp. More particularly, the term "appendage" denotes the hair, body hair and the nails, and more particularly the hair and body hair.

The epidermis is conventionally divided into a basal layer of keratinocytes that constitutes the germinal layer of the epidermis, a pluristratified "spinous" layer constituted of polyhedral cells positioned on the germinal layer, one to three "granular" layers constituted of flattened cells containing distinct cytoplasmic inclusions, keratohyalin granules, and finally an assembly of upper layers known as the cornified layers (or stratum corneum), constituted of keratinocytes at the terminal stage of their differentiation, known as corneocytes.

Corneocytes are anuclear cells mainly constituted of a fibrous material containing cytokeratins, surrounded by a cornified envelope. New keratinocytes undergo permanent production to compensate for the continual loss of epidermal cells from the cornified layer by a mechanism known as desquamation. The whole of the process resulting in the formation of the stratum corneum and its elimination is the subject of fine regulation under the control of multiple hormonal or cellular factors. An imbalance in these factors, if it is not rapidly regulated, ends up resulting in dysfunction of the proliferation and/or differentiation of the cells in the basal layer, or of desquamation.

Many defects or disorders of the skin and its appendages can be linked to such a modification.

Thus, when the proliferation and/or differentiation of the cells of the basal layer of the epidermis are accelerated relative to desquamation, then the stratum corneum tends to thicken. This dysfunction can, depending on its degree of manifestation, be associated with various esthetic defects, such as signs of skin aging, an epidermal barrier function disorder, or signs of dryness of the skin, or, where appropriate, with various pathological disorders, for instance hyperkeratosis, xerosis, ichthyosis, psoriasis or reactive hyperkeratosis.

Conversely, a slowing of the proliferation and/or differentiation of the cells of the basal layer relative to desquamation can manifest itself through thinning of the epidermis, and more particularly of the cornified layer. This dysfunction can, depending on its degree of manifestation, be associated with various esthetic defects, such as a healing defect, or a re-epithelialization defect, in particular after a skin scrubbing or exfoliant treatment, or, where appropriate, with various pathological disorders, for instance reactions of immune origin, generally induced by contact of the skin with one or more exogenous agents.

Various imbalances in the hormonal, cellular or molecular mechanisms underlying the formation of the stratum corneum can be associated with these disorders.

For example, FR 2 842 209 describes the expression of the SASPase protein in the epidermis, and its use as a target in the treatment of skin disorders. However, the detection of the expression of SASPase in the epidermis is only one element of the set of mechanisms involved in epidermal homeostasis, and many aspects of these mechanisms are still to be determined.

Thus, there is still a need to determine more precisely the nature and the role of the factors involved in epidermal homeostasis, and in particular in the proliferation and/or differentiation of the cells of the epidermis.

In particular, there is a need to determine the nature of the agents capable of modulating the proteolytic activity of SASPase.

There is still a need to identify and provide new cosmetic or therapeutic targets with regard to the skin and/or its appendages, and in particular which are involved in the proliferation and/or differentiation of the cells of the epidermis.

There is still a need to identify and provide new tools for screening for active compounds capable of modulating the proliferation and/or differentiation of the cells of the epidermis, which are simultaneously rapid, sensitive, easy to use and inexpensive.

The object of the present invention is to satisfy these needs.

Thus, according to a first subject, the present invention relates to an isolated peptide represented by an amino acid sequence chosen from SEQ ID NO: 9, SEQ ID NO: 16, a fragment thereof, or a homolog thereof having a sequence identity of at least 85%, and capable of modifying the three-dimensional conformation of a complex formed by interaction of a first amino acid sequence from filaggrin-2 with a second amino acid sequence from SASPase.

Unexpectedly, the inventors have demonstrated that filaggrin-2, in monomer or dimer form, and SASPase bind to one another by affinity so as to together form a protein complex. In particular, the inventors have identified, in filaggrin-2 and SASPase, the precise amino acid sequences involved in this binding and the formation of the protein complex.

What is more, the inventors have demonstrated that the binding of filaggrin-2 to SASPase increases the proteolytic activity of the latter, and that this activity can also be modulated by specific peptides from filaggrin-2.

For the purposes of the invention, the term "interaction" means the forming of one or more bonds by affinity between two amino acid sequences such that a protein or peptide complex capable of remaining stable under physiologically acceptable conditions is formed. In the present invention, the terms "interaction" and "association" are used without distinction.

For the purposes of the invention, the term "three-dimensional conformation" of a complex means the spatial arrangement of the amino acid sequences of which this complex is composed, taken together, when they interact with one another.

For the purposes of the invention, the term "modification" of the three-dimensional conformation of a complex means a modification of the spatial arrangement of the amino acid sequences in the complex or a modification of the three-dimensional structure of both or either of these sequences.

These modifications can result in a modification of the overall shape, also called allosteric modification, of the complex and/or in a modification of the thermodynamic equilibrium between the free amino acid sequences and the amino acid sequences bound to one another. These modifications result in an increase, a decrease or a stabilization of the biological activity of the complex.

Preferably, these modifications can result in a dissociation of a complex, i.e. a shift of the thermodynamic equilibrium established between the free sequences and the bound sequences, toward the free sequences.

According to yet another aspect, the present invention relates to a chimeric peptide comprising a first amino acid sequence fused to a second amino acid sequence, wherein the first amino acid sequence represents a peptide of the invention.

According to yet another aspect, the present invention relates to an isolated complex formed by interaction of a first amino acid sequence with a second amino acid sequence from a SASPase, or a homolog thereof having a sequence identity of at least 85%, wherein said first amino acid sequence represents a peptide of the invention, in particular as defined according to the first subject of the invention.

For the purposes of the invention, the expression "amino acid sequence from" aims to denote all or part, i.e. a fragment or the whole, of the protein or peptide under consideration.

According to yet another aspect, the present invention relates to the use of at least one complex of the invention for screening for compounds capable of regulating the proliferation and/or differentiation of the cells of an epidermis.

According to yet another aspect, the present invention relates to a method for screening for a compound capable of regulating the proliferation and/or differentiation of the cells of an epidermis, said method comprising at least the steps described hereinafter.

A method or use of the invention can advantageously be carried out in vivo, ex vivo or in vitro.

In particular, a method or use of the invention can be carried out, ex vivo or in vitro.

A screening method of the invention can advantageously be carried out in order to identify new active compounds capable of preventing and/or treating an esthetic defect or a pathological disorder of the skin and/or its appendages linked to a dysfunction of the differentiation and/or proliferation of the cells of the epidermis.

For the purposes of the present invention, the term "preventing" means reducing the risk or the probability of occurrence of a given phenomenon, i.e. in the present invention, an esthetic defect or a pathological disorder of the skin and/or its appendages linked to a defect in differentiation and/or proliferation of the cells of the epidermis.

The present invention advantageously makes it possible to provide a new target which is of use in the cosmetics industry or in therapy with regard to the skin and/or its appendages.

Advantageously, the peptides of the present invention can be particularly of use for carrying out a method for screening for new cosmetic or dermatological active agents, which is simple, inexpensive and sensitive.

Advantageously, the present invention can make it possible to identify new active agents capable of acting on an unknown pathway of the regulation of epidermal homeostasis and thus to provide a more precise effect and better effectiveness with regard to cosmetic defects or pathological disorders of the skin and/or its appendages.

The present invention advantageously makes it possible to provide a novel screening tool which is particularly effective and sensitive for the detection of new active compounds that are of use in the cosmetics industry or in therapy with regard to the skin and/or its appendages.

These active compounds can in particular be effective with respect to esthetic defects or pathological disorders of the skin and/or its appendages linked to a defect in proliferation and/or differentiation of the cells of the epidermis.

Advantageously, the peptides of the present invention can also be of use as a cosmetic active agent.

Peptides

The peptides of the invention may be from, or derived from, the amino acid sequences of SASPase or of FLG2, and are capable, under appropriate conditions, of modifying the three-dimensional conformation of a complex formed by interaction of a first amino acid sequence from filaggrin-2 with a second amino acid sequence from SASPase.

Such a complex can be formed by interaction of all or part of a first amino acid sequence from SASPase with all or part of a second amino acid sequence from FLG2 or a dimer of this second sequence.

The amino acid sequences of SASPase or of FLG2 which are suitable for such a complex can, in particular, be represented by sequences chosen from sequences represented by the references Q53RT3 and Q5D862 (Uniprot/Swissprot references), fragments thereof, or homologs thereof having a sequence identity of at least 85%, and a biological activity of the same nature.

According to one embodiment, a peptide of the invention can be capable of binding by affinity to an amino acid sequence from SASPase. An amino acid sequence from SASPase which is more particularly under consideration according to the invention may be the amino acid sequence represented by the Q53RT3 sequence (Uniprot/Swissprot ref.), and preferably the amino acid sequence extending from positions 85 to 343 of this sequence. The amino acid sequence extending from positions 85 to 343 of the Q53RT3 sequence is presumed to represent an active form of SASPase comprising 259 amino acids, giving a molecular weight of approximately 28 kDa.

A peptide of the invention may be from FLG2. In particular, a filaggrin-2 which is suitable for the invention may be human filaggrin-2, and more particularly a filaggrin-2 having the amino acid sequence represented by the reference Q5D862 (Uniprot/Swissprot ref.). This sequence comprises 2391 amino acids, and has a molecular weight of approximately 948 kDa.

According to one preferred embodiment variant, the invention relates to an isolated peptide of amino acid sequence represented by the sequence SEQ ID NO: 9, a fragment thereof, or a homolog thereof having a sequence identity of at least 85%. Such a peptide is capable of binding by affinity to an amino acid sequence from a SASPase.

The amino acid sequence represented by SEQ ID NO: 9 represents the amino acid sequence extending from positions 2 to 95 of the sequence of the reference Q5D862 of filaggrin-2.

According to one embodiment, a peptide of the invention may in particular be constituted of from 3 to 50 contiguous amino acids, preferably from 6 to 30 contiguous amino acids, preferably from 8 to 20 contiguous amino acids and more preferably from 8 to 16 contiguous amino acids, or even from 10 to 16 contiguous amino acids, from the sequence SEQ ID NO: 9.

More preferably, a peptide of the invention may in particular be constituted of from 3 to 10 contiguous amino acids from the sequence SEQ ID NO: 9. Such peptides may more particularly be suitable for cosmetic use, for example in cosmetic compositions applied topically or transdermally.

According to one preferred embodiment variant, a peptide of the invention can be represented by an amino acid sequence chosen from SEQ ID NO: 10, SEQ ID NO: 11, SEQ ID NO: 12, SEQ ID NO: 13, SEQ ID NO: 14, SEQ ID NO: 15, a fragment thereof, or a homolog thereof having a sequence identity of at least 85%.

These peptides are capable of binding by affinity to an amino acid sequence from a SASPase.

According to another embodiment, a peptide of the invention can be capable of binding by affinity to an amino acid sequence from FLG2. An amino acid sequence from FLG2 which is more particularly under consideration according to the invention may be the amino acid sequence represented by the Q5D862 sequence (Uniprot/Swissprot ref.), and preferably the amino acid sequence extending from positions 2 to 213 of this sequence.

According to one embodiment variant, a peptide of the invention can be capable of binding to a dimer of an amino acid sequence from FLG2.

According to another embodiment, a peptide of the invention capable of binding by affinity to an amino acid sequence from FLG2 may be from SASPase. A SASPase or "Skin ASPartic protease" which is suitable for the invention may be human SASPase, and more particularly may be a SASPase having the amino acid sequence represented by the reference Q53RT3 (Uniprot/Swissprot ref.). This sequence comprises 343 amino acids and has a molecular weight of approximately 37 kDa.

According to one preferred embodiment variant, the invention relates to an isolated peptide of amino acid sequence represented by SEQ ID NO: 16, a fragment thereof, or a homolog thereof having a sequence identity of at least 85%. Preferably, such a peptide may be capable of binding by affinity to an amino acid sequence from an FLG2.

The amino acid sequence represented by SEQ ID NO: 16 represents the amino acid sequence extending from positions 97 to 173 of the Q53RT3 sequence of SASPase (Uniprot/Swissprot ref.).

According to one embodiment, a peptide of the invention capable of binding by affinity to an amino acid sequence from a SASPase can be encoded by a nucleic acid sequence represented by a sequence chosen from SEQ ID NO: 1, a fragment thereof, or a homolog thereof having a sequence identity of at least 85%.

Preferably, a peptide of the invention capable of binding by affinity to an amino acid sequence from a SASPase can be encoded by a nucleic acid sequence represented by SEQ ID NO: 1, SEQ ID NO: 2, SEQ ID NO: 3, SEQ ID NO: 4, SEQ ID NO: 5, SEQ ID NO: 6, SEQ ID NO: 7, a fragment thereof, or a homolog thereof having a sequence identity of at least 85%.

According to one embodiment, a peptide of the invention capable of binding by affinity to an amino acid sequence from an FLG2 can be encoded by a nucleic acid sequence represented by a sequence chosen from SEQ ID NO: 8, a fragment thereof, or a homolog thereof having a sequence identity of at least 85%.

According to one of its aspects, the invention also relates to an isolated nucleic acid sequence encoding a peptide of the invention, a fragment thereof, or a homolog thereof having a sequence identity of at least 85%, and in particular as defined previously.

A nucleic acid sequence of the invention can be used for the preparation of any of the amino acid sequences of the invention, and more particularly for the preparation of a chimeric peptide as indicated hereinafter.

A nucleic acid sequence which is suitable for the invention can be of any possible origin, namely animal, in particular mammalian and even more particularly human, or plant, or from microorganisms, such as viruses, phages, bacteria or else fungi, without any preconception as to whether or not they are naturally present in said organism.

The term "homolog" of an amino acid sequence or a nucleic acid sequence is intended to denote a sequence having an identity of at least 85%, in particular of at least 90%, in particular of at least 98% and more particularly of at least 99%, with said sequence, and having a biological activity of the same nature.

A sequence homology can be identified by any technique normally used in the field by those skilled in the art. By way of example, a sequence homology can be determined by using the BLAST computer interface available on the NCBI website, configured with the default parameters.

A homolog of an amino acid sequence can differ from this sequence, for example, by one or more deletion(s) and/or insertion(s) and/or one or more substitution(s) of an amino acid. Similarly, a homolog of a nucleic acid sequence can differ from this sequence, for example, by one or more deletion(s) and/or insertion(s) and/or one or more substitution(s) of a base or of a codon. These modifications can be combined.

According to one embodiment variant, a homolog of an amino acid or nucleic acid sequence can comprise one or more conservative amino acid or codon substitutions.

A conservative substitution is the replacement, in a sequence, of one amino acid with another amino acid which has physicochemical properties that are substantially similar or sufficiently close to those of the amino acid of origin for the properties and functions of the protein or of the peptide not to be affected or not to be substantially affected. Likewise, a conservative substitution is the replacement, in a nucleic acid sequence, of one codon with another codon encoding an amino acid which is identical or which has physicochemical properties that are substantially similar or sufficiently close to those of the amino acid of origin for the properties and functions of the nucleic acid sequence encoded not to be affected or not to be substantially affected.

The modifications of the amino acid or nucleic acid sequences presented above can be generally referred to as a "mutation". Thus, the homologs of the invention also relate to the mutants and the variants of the amino acid or nucleic acid sequences of the invention.

According to one embodiment, an amino acid sequence from SASPase can comprise one or more mutations.

By way of example of SASPase mutations which can be considered in the present invention, mention may be made of the replacement of one or more amino acid residues with amino acid residues having a similar hydropathic index, without however substantially affecting the biological properties of the SASPase, and in particular its property of interaction with its partner peptide. The hydropathic index is an index assigned to amino acids according to their hydrophobicity and their charge (Kyte & Doolittle, J. Mol. Biol., 1982, 157: 105).

An amino acid sequence which is suitable for the invention can comprise one or more post-translational modification(s).

The expression "post-translational modification(s)" is intended to encompass all the modifications that an amino acid sequence is liable to undergo at the end of its synthesis in a cell, such as, for example, one or more phosphorylation(s), one or more glycosylation(s), one or more citrullination(s), one or more lipidation(s), such as a farnesylation or a palmitoylation, or a structural rearrangement such as disulfide bridge formation and/or cleavage within the peptide sequence.

The expression "biological activity of the same nature" of an amino acid sequence of the invention means, in particular, its ability to bind by affinity with a partner amino acid sequence. The expression "biological activity of the same nature" of a nucleic acid sequence means, in particular, its ability to be transcribed and translated into an amino acid sequence.

According to one embodiment variant, with regard to SASPase, a biological activity of the same nature can also be understood to be its proteolytic activity, in particular with regard to corneodesmosin.

According to another embodiment variant of the invention, when an inactive mutant of SASPase is used, the expression "biological activity of the same nature" means principally the property of the mutant of binding by affinity to an amino acid sequence of the invention from FLG2.

Thus, a SASPase amino acid sequence which is suitable for the invention necessarily has at least the property of interacting with an FLG2 amino acid sequence.

With regard to an amino acid sequence from FLG2, a biological activity of the same nature can also be understood to be its property of promoting and/or increasing the proteolytic activity of SASPase.

According to another variant of the invention, a biological activity of the same nature can also be understood to be the biological activity of a complex of the invention with regard to the proliferation and/or differentiation of the cells of the epidermis.

For the purposes of the invention, the term "fragment" of an amino acid sequence means any portion which is from this sequence and constituted of from 3 to 50 contiguous amino acids, preferably from 6 to 30 contiguous amino acids, preferably from 8 to 20 contiguous amino acids and more preferably from 10 to 16 contiguous amino acids, and which has a biological activity of the same nature as that expressed by the amino acid sequence.

The term "fragment" with regard to a nucleic acid sequence denotes any portion which is from this sequence and constituted of from 9 to 150 bases, preferably from 18 to 90 bases, preferably from 24 to 60 bases and more preferably from 30 to 48 bases, and which encodes a fragment of the amino acid sequence encoded by said sequence.

According to one embodiment, an amino acid sequence of the invention can be a natural or synthetic amino acid sequence, where appropriate capable of being obtained by chemical or biological synthesis, or by extraction from a biological tissue, for instance the skin, which naturally or after transduction expresses an amino acid sequence, and also the various post-translational forms thereof.

A peptide of the invention can also be chosen from peptidomimetics. A peptidomimetic of the invention can be obtained by modification of an amino acid sequence of the invention, or by synthesis of a compound which mimics such a sequence, such as a peptoid or a β-peptide. The modifications considered can be based on the introduction of "unnatural" changes into the amino acid sequence, such as modifications of the backbone or the integration of unnatural amino acids.

A subject of the present invention is also a chimeric peptide comprising a first amino acid sequence fused or coupled with a second amino acid sequence, a hydrophilic or hydrophobic targeting agent, a bioconversion precursor, and an affinity label, for example a fluorescent label, a luminescent label, a radioactive label or a colorimetric label.

In a nonlimiting manner, mention may be made, as examples of compounds which can be coupled to an amino acid sequence of the invention, of fluorescent proteins such as Green Fluorescent Protein, fluorescent chemical compounds, such as rhodamine, fluorescein or Texas Red, phosphorescent compounds, radioactive elements, such as $^{3}$H, $^{35}$S, $^{99}$Tc, $^{121}$I or $^{125}$I, or colorimetric labels such as chromogenic substrates sensitive to the action of galactosidase, of peroxidase, of chloramphenicol acetyltransferase, of luciferase or of alkaline phosphatase, or else affinity labels, in particular of Histag, GST or MBP type.

Depending on the nature of the compounds which can be coupled with an amino acid sequence of the invention, the coupling can be carried out by any chemical method or any molecular biology method known to those skilled in the art. In the latter case, reference is made to a fusion peptide or protein, or a chimeric peptide or protein.

Thus, a subject of the present invention is also a chimeric peptide comprising a first amino acid sequence fused to a second amino acid sequence, wherein the first amino acid sequence represents a peptide of the invention as defined previously.

According to one embodiment, a chimeric peptide according to the invention can comprise, as second amino acid sequence, a sequence chosen from a fluorescent protein, an affinity label, a signal peptide and a propenetrating peptide, and is preferably an affinity label.

According to one embodiment, a first amino acid sequence of a chimeric peptide of the invention may be an amino acid sequence from an FLG2 or from a SASPase, and more preferentially from the sequences SEQ ID NO: 9 or SEQ ID NO: 16.

By way of a preferred second amino acid sequence of a chimeric peptide of the invention, mention may be made of fluorescent proteins, and in particular GFP (Green Fluorescent Protein), ECFP (Enhanced Cyan Fluorescent Protein), DsRed2FP (DsRed fluorescent protein), EGFP (Enhanced Green Fluorescent Protein), EYFP (Enhanced Yellow Fluorescent Protein) and EBFP (Enhanced Blue Fluorescent Protein).

By way of an affinity label suitable for the invention, mention may in particular be made of glutathione-S-transferase (GST), maltose binding protein (MBP), thioredoxin (THX), a Myc label, a FLAF label, a His label, or a THX-His-tag or THX-His-S-tag label.

A chimeric peptide of the invention can be obtained by any molecular biology method known to those skilled in the art, in particular as described by Sambrook et al. (Molecular Cloning: A laboratory Manual, Ed. Cold Spring Harbor, 2001).

According to another of its aspects, the invention relates to an isolated complex formed by interaction of a first amino acid sequence with a second amino acid sequence from a SASPase, or a homolog thereof having a sequence identity of at least 85%, wherein said first amino acid sequence represents a peptide from FLG2, and preferably as defined previously.

According to one preferred embodiment variant, a second amino acid sequence of a complex of the invention can represent a peptide from a SASPase as defined previously.

Screening

The present invention relates to the use of at least one complex of the invention for screening for compounds capable of regulating the proliferation and/or differentiation of the cells of an epidermis.

According to one embodiment, the invention relates to a method for screening for a compound capable of regulating the proliferation and/or differentiation of the cells of an epidermis.

Preferably, such a compound can modulate the three-dimensional conformation of a complex formed by interaction of a first amino acid sequence from FLG2, or of a dimer of such a sequence, with a second amino acid sequence from SASPase.

More preferably, such a compound can modulate the formation of a complex formed by interaction of a first amino acid sequence from FLG2, or of a dimer of such a sequence, with a second amino acid sequence from SASPase.

Advantageously, the amino acid sequences of FLG2 and of SASPase can be as defined previously.

According to one embodiment variant, a complex under consideration may be a complex of the invention as defined previously.

A method of the invention may comprise at least the steps consisting in:

a) providing a complex of the invention under conditions favorable to its formation, b) associating, prior to or subsequent to step a), the first and/or the second amino acid sequence(s) with an entity, the first and/or the second amino acid sequence(s) forming, with said entity, an assembly capable of emitting a signal after exposure to an excitation wavelength, and the implementing of steps a) and b) resulting in the obtaining of said complex, c) subjecting said complex to said excitation wavelength so as to obtain a first signal S1 characteristic of the complex, d) quantitatively or qualitatively determining the signal S1, e) bringing the complex into contact with a medium presumed to contain a compound to be screened, f) subjecting the medium obtained in step e) to the excitation wavelength so as to obtain a second signal S2, g) quantitatively or qualitatively determining the signal S2, and h) comparing the first and second signals S1 and S2 so as to draw a conclusion relating to a possible modification of the three-dimensional conformation of the complex in the presence of the compound screened.

According to one embodiment, an entity which is suitable for the invention can be chosen from a support which is suitable for surface plasmon resonance, a fluorescent label, an antibody or a combination of primary and secondary antibodies, said antibody or said secondary antibody bearing a fluorescent label.

A first and/or a second amino acid sequence of the invention can be associated with an entity by any method known to those skilled in the art, and adapted to the nature of the support to the first and/or the second of amino acids must be associated. A coupling method will naturally be chosen so as not to affect the binding or affinity properties of the amino acid sequences used.

According to one embodiment, an association between a first and/or a second amino acid sequence can be carried out by chemical coupling, by molecular biology, or by specific strong-affinity interaction(s).

In particular, an association can be carried out by chemical coupling, in particular by means of reactive chemical functions, or by a molecular biology method.

When an association via a chemical method is carried out, the chemical functions to be reacted may be naturally present on the first and/or the second amino acid sequences, or may be introduced onto the first and/or the second amino acid sequences and the entity prior to the chemical reaction.

By way of example of the reactive chemical functions which are suitable for the invention, mention may, for example, be made of those conventionally used in "click chemistry" reactions.

By way of example of a molecular biology method which is suitable for the association between an entity and the first and/or the second amino acid sequences, mention may be made of those conventionally used in cloning methods comprising, in particular, the preparation of appropriate nucleic acid sequences, their ligation and their introduction into a suitable expression vector, for example a plasmid, and the transfection of the plasmid into a host cell capable of allowing the expression and the production of a chimeric peptide of the invention.

According to another embodiment, an entity and the first and/or the second amino acid sequences can be associated with one another by means of one or more specific strong-affinity interaction(s).

According to one embodiment, an entity which is in particular suitable for the invention may be an antibody or a set of primary and secondary antibodies.

An antibody which is suitable for the invention can be obtained by any method known to those skilled in the art, in particular as described in "Antibodies: A Laboratory Manual", Cold Spring Harbor Laboratory Press, Cold Spring Harbor, N.Y. (1990).

By way of the type of antibody which is suitable for the invention, mention may be made of monoclonal or polyclonal antibodies, and also immunoglobulin fragments capable of binding an antigen and which can be produced by any genetic engineering technique known to those skilled in the art or by enzymatic or chemical cleavage of whole antibodies.

More particularly, an antibody which is suitable for the invention can be chosen from a monoclonal antibody, a polyclonal antibody, a diabody, an scFv antibody, a F(ab')$_2$ antibody, a Fab' antibody, a chimeric antibody, a humanized antibody and a recombinant antibody.

According to one embodiment, an antibody which is suitable for the invention may have an affinity for a part of the first and/or of the second amino acid sequences against which it is directed, or for a specific affinity label borne by the first and/or the second amino acid sequences.

According to one embodiment of the present invention, the first and/or the second amino acid sequences can bear an affinity label recognized by an antibody.

An affinity label which is suitable for the invention can in particular be chosen from the affinity labels previously indicated.

By way of examples of antibodies which are suitable for the invention, mention may in particular be made of those used in the examples set out hereinafter.

According to another embodiment, the first and/or the second amino acid sequences are associated, respectively, with a first entity and a second entity, said entities comprising, respectively, a fluorescent group A and a fluorescent group B, said groups A and B defining a fluorescence energy acceptor-donor pairing which is suitable for the implementation of energy transfer by fluorescence resonance.

By way of examples of acceptor-donor pairings which may be used according to the present invention, mention may be made, in a nonlimiting manner, of the BFP (Blue Fluorescent Protein)/GFP (Green Fluorescent Protein), CFP (Cyan Fluorescent Protein)/YFP (Yellow Fluorescent Protein), CFP/DsRed (Red Fluorescent Protein), GFP/DsRed and EuK (Europium Cryptate)/XL665 pairings. Preferably, an acceptor-donor pairing which is suitable for the invention may be EuK/XL665.

According to one embodiment variant, the first and second entities may be fluorescent labels. Such fluorescent labels may be chosen from fluorescent molecules or fluorescent proteins normally used in the field. Preferably, the fluorescent labels used may be chosen from fluorescent proteins fused by molecular biology, in particular as indicated previously, to the first and/or to the second amino acid sequence.

According to another embodiment variant, the first and second entities may be antibodies bearing fluorescent labels and may be capable of binding, respectively, to a first and a second affinity label borne, respectively, by the first and/or the second amino acid sequence.

According to one embodiment, the signal S1 quantitatively or qualitatively determined in step d) of the method according to the invention may be a fluorescent signal obtained by irradiation at an excitation wavelength for the fluorescence energy donor.

The signal S2 quantitatively or qualitatively determined in step g) of the method may be a fluorescent signal obtained by irradiation at an excitation wavelength for the fluorescence energy donor.

The fluorescence signals S1 and S2 can be measured using any device suitable for the invention and known to those skilled in the art. By way of examples of devices which are suitable for the invention, mention may be made of a microplate reader, a fluorescence microscope, a spectrofluorometer or a fluorescence scanner.

According to one preferred embodiment, a method of the invention can be carried out at high-throughput, in microplates, and the fluorescence signals can be measured by means of a microplate reader, for example a Pherastar reader (BMG).

A signal S2 significantly higher than the signal S1 in the presence of a compound to be screened may be an indication of a compound which promotes the equilibrium and the stability of the three-dimensional conformation of a complex of the invention.

Preferably, such a compound can promote, or be an agonist of, the interaction between the first and the second amino acid sequences.

Conversely, a signal S2 significantly lower than the signal S1 in the presence of a compound to be screened may be an indication of a compound which destabilizes or modifies the three-dimensional conformation of a complex of the invention.

Preferably, such a compound can destabilize, or be an antagonist of, the interaction between the first and the second amino acid sequences.

A method according to the invention makes it possible to screen for an agent that modulates the proliferation and/or differentiation of the cells of the epidermis.

For the purposes of the invention, the expression "modulating compound" means any compound liable to act or capable of acting, directly or indirectly, on a complex comprising an association of a first amino acid sequence from FLG2, or of a dimer of this sequence, with a second amino acid sequence from SASPase for the purpose of modulating the three-dimensional conformation of this association.

According to one embodiment of the invention, a screened compound may be an agonist or an antagonist of this association.

According to one embodiment variant, a modulating compound may promote, or be an agonist of, this association. Alternatively, according to another embodiment variant, a modulating compound may be a compound which destabilizes, or which is an antagonist of, this association.

The agonist or antagonist nature of a modulating compound with regard to this association will be more particularly selected according to the modulating effect to be exerted on the proliferation and/or differentiation of the cells of the epidermis.

Thus, depending on the nature of the esthetic defect or of the pathological disorder of the skin and/or its appendages to be prevented or treated, a modulating compound which is an agonist or an antagonist of this association will more particularly be used.

According to one preferred embodiment of the invention, a screened compound may be capable of preventing and/or treating an esthetic defect or a pathological disorder of the skin and/or its appendages linked to a dysfunction of the differentiation and/or proliferation of the cells of the epidermis.

According to one embodiment, a screening method of the invention may also comprise at least one additional step consisting in evaluating the property of a screened compound of modulating the differentiation and/or proliferation of the cells of an epidermis.

Such an evaluation can be carried out in vitro or ex vivo, in particular on epidermal cells in culture. The cells may be cells in lines, i.e. transformed with a virus or of tumor origin in order to immortalize them.

Alternatively, the cells may be primary culture cells, i.e. cells from a tissue taken from a living organism, for example an epidermis from a human being.

Preferably, the cells in culture may be fibroblasts, or even keratinocytes, which are in particular stratified. The cell cultures can be prepared according to any method known to those skilled in the art.

Likewise, an in vitro evaluation may be carried out on a reconstructed epidermis model. Such epidermis models may be commercially available, for example such as the EPISKIN® model.

The in vitro or ex vivo evaluation of a compound screened according to the invention may be carried out by any protocol known to those skilled in the art aimed at comparing the effect given by a test compound with a control or standard value.

The effect of a compound screened according to the invention, in vitro or ex vivo, can be determined by measuring biological markers known to be specifically associated with the differentiation and/or proliferation of the cells of an epidermis.

Such markers can be chosen, for example, from the measurement of the thickness of the stratum corneum, the measurement of its barrier function, and the measurement of the expression and/or of the activation of transglutaminase I, of filaggrin, of caspase 14, of SASPase, of corneodesmosin, of desmoglein or of the Ki67 protein.

These markers can be determined, for example, by Western blotting or immunofluorescence according to any protocol known to those skilled in the art.

Uses and Compositions

A screened compound, a peptide or a nucleic acid sequence of the invention may be used in the cosmetics industry as a cosmetic active agent for preventing and/or treating an esthetic defect of the skin and/or its appendages linked to a dysfunction of differentiation and/or proliferation of the cells of an epidermis.

A screened compound, a peptide or a nucleic acid sequence of the invention may be used for the preparation of a therapeutic composition intended for preventing and/or treating a pathological disorder of the skin and/or its appendages linked to a dysfunction of differentiation and/or proliferation of the cells of an epidermis.

Likewise, the invention relates to a therapeutic composition comprising, as active agent, a screened compound, a peptide or a nucleic acid sequence of the invention for preventing and/or treating a pathological disorder of the skin and/or its appendages linked to a dysfunction of differentiation and/or proliferation of the cells of an epidermis.

The cosmetic or therapeutic application of a screened compound, a peptide or a nucleic acid sequence of the invention depends on the nature, or even on the degree or on the strength of manifestation of the signs expressed by the skin and/or its appendages subsequent to a dysfunction of differentiation and/or proliferation of the cells of an epidermis. It is within the general knowledge of those skilled in the art to assess this nature or this strength of manifestation and to implement the appropriate application.

One particular embodiment of the invention relates to the cosmetic use of a peptide of the invention or of a nucleic acid sequence encoding such a peptide, as a cosmetic active agent for preventing and/or treating an esthetic defect of the skin and/or its appendages linked to a dysfunction of the differentiation and/or proliferation of the cells of an epidermis.

An esthetic defect considered by the invention may be chosen from signs of skin aging, an epidermal barrier function disorder, signs of dryness of the skin, cutaneous signs of hyperseborrhea, a modification of the complexion of the skin, a skin or scalp desquamation disorder, and a healing and/or re-epithelialization defect.

An esthetic defect considered by the invention may also be hyperhidrosis and/or a body odor problem.

According to another embodiment, a peptide or a nucleic acid sequence of the invention may also be used in the cosmetics industry as an active agent for promoting re-epithelialization after a skin scrubbing or exfoliant treatment.

According to another embodiment, a peptide or nucleic acid sequence according to the invention may be used in the cosmetics industry as an active agent for preventing and/or treating hair loss and/or promoting hair restoration, or preventing the regrowth of body hair.

According to one embodiment, a pathological disorder may be chosen from cancer, psoriasis, vitiligo, rosacea, atopic dermatitis, seborrheic dermatitis and acne.

According to one embodiment, a cosmetic use of the invention may preferably employ a peptide of the invention from FLG2 and capable of binding by affinity to an amino acid sequence from a SASPase or a nucleic acid sequence encoding such a peptide, in particular as defined previously, as a cosmetic active agent for preventing and/or treating the aging of an epidermis and/or improving the barrier function of an epidermis.

According to one embodiment, a cosmetic use of the invention may preferably employ a peptide of the invention from SASPase and capable of binding by affinity to an amino acid sequence from a filaggrin-2, in particular as defined previously, as a cosmetic active agent for preventing and/or treating the aging of an epidermis and/or improving the barrier function of an epidermis.

According to one of its aspects, the invention relates to a cosmetic composition comprising, in a physiologically acceptable medium, an effective amount of at least one peptide of the invention or of a nucleic acid sequence encoding such a peptide.

According to one of its aspects, the present invention relates to a cosmetic or therapeutic composition comprising an effective amount of at least one peptide of the invention or a nucleic acid sequence encoding such a peptide, as an active agent for treating and/or preventing an esthetic defect or a pathological disorder of the skin and/or its appendages linked to a dysfunction of the proliferation and/or differentiation of the cells of the epidermis.

For the purposes of the present invention, the expression "effective amount" means an amount of an active agent that is sufficient and necessary for exerting a prevention and/or treatment effect with regard to an esthetic defect or a pathological disorder of the skin and/or its appendages.

Such a composition may be administered orally, parenterally or topically.

Such implementation routes are known to those skilled in the art.

According to another of its aspects, the present invention relates to a composition comprising at least one nucleic acid sequence encoding a peptide of the invention.

Such a composition can be devoted to allowing the expression of a peptide of the invention in a cell, biological tissue or an organ.

Such a composition can be used for cosmetic, therapeutic or diagnostic purposes.

According to another aspect, the present invention relates to a cosmetic treatment process for preventing and/or treating an esthetic defect of the skin and/or its appendages linked to a dysfunction of the differentiation and/or proliferation of the cells of the epidermis in an individual, comprising at least one step of administering, to said individual, as an active agent, an effective amount of at least one peptide or of a nucleic acid sequence of the invention.

Such a process can advantageously be carried out topically, orally or parenterally, and in particular topically or orally.

The parenteral route comprises in particular the intradermal route and the subcutaneous route.

According to another aspect, the present invention relates to the use of an effective amount of at least one peptide of the invention or of at least one nucleic acid sequence of the invention or of at least one screened compound of the invention, for preparing and/or improving a pluristratified cell model, in particular of epidermal or mucosal type, and in particular a reconstructed skin model.

Advantageously, a peptide or a nucleic acid sequence of the invention or a screened compound of the invention is added to the culture medium in which the pluristratified culture model is cultured. The cell model culture step and duration of incubation carried out in the presence of an amino acid or nucleic acid sequence of the invention or of a screened compound of the invention are naturally adapted by those skilled in the art according to the cell model to be obtained and to the effect to be obtained.

For the purposes of the invention, the expression "reconstructed skin model" is intended to denote a model in which various cell types are combined, such as, in particular, the cells naturally present in skin, like, for example, keratinocytes, fibroblasts, Langerhans cells and melanocytes. The cells of fibroblast type can optionally be irradiated.

Such models and the preparation thereof are known to those skilled in the art.

In the description and in the examples that follow, unless otherwise indicated, the percentages are weight percentages and the ranges of values written in the form "between . . . and . . ." include the stated lower and upper limits.

The examples given below are presented as nonlimiting illustrations of the invention.

EXAMPLES

Example 1

SASPase-FLG2 Interaction and Identification of the Peptide Domains Involved in the Interaction A first study using the "double-hybrid" technique was carried out using the whole 28 kDa SASPase protein in its wild-type form (SASPase_28, GENBANK Ref. gi16553767)

and in its form mutated at the catalytic aspartic acid (SASPase_28$_{D128A}$), and also the 37 kDa SASPase form (SASPase_37), in its whole form (GENBANK Ref. gi189409121), and a fragment corresponding to the N-terminal end of 84 amino acids of the protein relative to the sequence of SASPase_28 (SASPase_27$_{N84}$).

The SASPase sequences were fused to a DNA-binding domain, LexA, according to the orientation N-LexA-SASPase-C, so as to keep the C-terminal end of the SASPase free, with the exception of the SASPase_28$_{N84}$ sequence which is fused to the LexA domain according to the orientation N-SASPase_28$_{N84}$-LexA-C.

The prey sequences were fused to the Gal4 transcription-activating domain.

SASPase_28, wild-type or mutated, SASPase_37 and SASPase_28$_{N84}$ did not exhibit self-activation of the double-hybrid system. The screens carried out with the SASPase_28 or SASPase_37 sequences therefore made it possible to identify an interaction with filaggrin-2 (FLG2), with a very good confidence score.

The interaction with a SASPase was found using, as bait, the filaggrin-2 fragment identified as interacting with the SASPase_28 and SASPase_37 sequences, and corresponding to amino acids 2-213 of the Genbank sequence: gi:62122916.

The sequence was fused to the DNA-binding domain, LexA, according to the orientation N-LexA-FLG2$_{2-213}$-C.

The prey sequences were fused to the Gal4 transcription-activating domain.

The N-terminal fragment of filaggrin-2 exhibited a slight self-activation of the double-hybrid system, and a 3-aminotriazole concentration of 5 mM was therefore used for the screen.

The screen made it possible to confirm the interaction with SASPase.

Supplementary experiments were carried out in order to reduce and identify the size of the sequences responsible for this interaction between SASPase_28 and filaggrin-2.

These experiments made it possible to show that an N-terminal fragment of SASPase_28 (amino acids 11-86, SEQ ID NO: 16) was sufficient for the interaction with FLG2.

With regard to FLG2, these supplementary experiments showed that the N-terminal S100 domain of filaggrin-2 (amino acids 2-95, SEQ ID NO: 9) is involved in the interaction with SASPase.

Example 2

Modulation of the Proteolytic Activity of SASPase by FLG2

A recombinant filaggrin-2 (FLG2), constituted of the amino acids extending from positions 2 to 213 of the sequence represented by the reference Q5D862 (Ref.: Uniprot/Swissprot) fused to a Thioredoxin-His-S.Tag (THX-His-S-tag) affinity label was prepared in the parental plasmid pET32c (Novagen) (FLG2$_{2-213}$-Thioredoxin-His-S.Tag or FLG2-HS).

A recombinant 28 kDa SASPase (SASPase_28) constituted of the amino acids extending from positions 85 to 343 of the sequence represented by the reference Q53RT3 (Uniprot/Swissprot Ref.) was prepared as described by Bernard et al., (J. Invest. Dermatol., 2005, 125: 278-287).

SASPase_28 at 0.025 mg/ml is in the presence of a colorimetric substrate, Dabcyl-QIDRIMEK-Edans, at 0.01 mM (Production Jerini Peptide Ref. D17: JPT Peptide Technologies GmbH) in a PBS buffer.

FLG2-Hs is used at 0.01, 0.02, 0.04, 0.08, 0.16, 0.31, 0.63, 1.25, 2.5, 5 or 10 times the final concentration of SASPase (0.025 mg/ml).

The hydrolysis of the colorimetric substrate by the activated SASPase results in the separation of the EDANS fluorochrome and of its deactivator (or quencher) Dabcyl, and in an increase in the EDANS fluorescence.

The fluorescent signal is measured at $\lambda_{ex}$ 340 nm/$\lambda_{em}$ 490 nm. The fluorescence is read every 10 minutes for 1 h 30 min, at 37° C., with a SPECTRAMAX M5e (Molecular Devices).

The results obtained show that the enzymatic activity of SASPase is significantly increased in the presence of an increasing concentration of FLG2-Hs.

Peptides of 8 to 20 amino acids were synthesized using the amino acid sequence extending from positions 71 to 90 of FLG2, SEQ ID NO: 9.

The previous enzymatic assay was repeated with FLG2-Hs being replaced with each of the peptides thus prepared.

Among the peptides tested, the peptides represented by the sequences SEQ ID NO: 10, SEQ ID NO: 11, SEQ ID NO: 12, SEQ ID NO: 13, SEQ ID NO: 14 and SEQ ID NO: 15 were shown to have a particularly significant ability to increase the catalytic activity of SASPase.

Example 3

Screening for Agents that Modulate the Interaction between a Peptide from FLG2 and SASPase A method according to the invention can use the homogeneous time-resolved fluorescence (or HTRF) technique.

An amino acid sequence from SASPase (SEQ ID NO: 16) fused at its C-terminal end with the GST (Glutathione S-Transferase of *Schistosoma japonicum*) affinity label is prepared in the pGEX-4-T3 vector (GenBank U13855) SASPase$_{SEQ\ ID\ NO:\ 16}$-GST).

An amino acid sequence from FLG2 (SEQ ID No.: 9 SEQ ID NO: 9) fused at its N-terminal end with the Thioredoxin-His-S.Tag affinity label is prepared as follows FLG2$_{SEQ\ ID\ NO:\ 9}$-His-THX).

The plasmids obtained are used to transform competent *E. coli* bacteria. The transformed bacteria are then induced in the presence of IPTG and then centrifuged and lysed by ultrasound. The chimeric peptides are purified by affinity for the HIS or GST tag on an appropriate resin, and then dialyzed against a buffer. The chimeric peptides obtained are then assayed by the Bradford method.

Antibodies which recognize, respectively, the GST or His-S.Tag affinity labels, and which bear, respectively, an EuK fluorescence donor group (europium cryptate $\lambda_{ex}$ 337 nm/$\lambda_{em}$ 620 nm) or an XL1665 fluorescence receiver group ($\lambda_{ex}$ 570-630 nm/$\lambda_{em}$ 665 nm) are used to monitor the peptide-SASPase interaction.

Such antibodies are commercially available, for example from the company Cisco under the references 61GSTKLB (anti-GST K antibody) or 61HISKLB (anti-6HIS K antibody).

The SASPase$_{SEQ\ ID\ NO:\ 16}$-GST/FLG2$_{SEQ\ ID\ NO:\ 9}$-His-THX interaction is observed by fluorescence energy transfer (FRET) between the EuK and XL1665 fluorescent labels. The EuK fluorescence donor is excited at $\lambda_{ex}$ 337 nm and the emission of fluorescence from the XL1665 fluorescence acceptor is measured at $\lambda_{em}$ 665 nm.

The EuK fluorescence emission at $\lambda_{em}$ 620 nm, which takes place independently of the interaction between the peptides, is used to standardize the signal.

The screening method is carried out in 384-well plates by means of a Janus automated device from Perkin Elmer in a PBS phosphate buffer at pH 7.4.

A buffer, or a diluted solution, free of compound to be screened, is used as a control.

The SASPase$_{SEQ\ ID\ NO:\ 16}$-GST and the compound tested are preincubated, then the FLG2$_{SEQ\ ID\ NO:\ 9}$-His-THX is added to the incubation medium.

The antibodies specific for the affinity labels are then added to the incubation medium.

The mixture is left to incubate before reading the fluorescence ($\lambda_{ex}$ 337 nm/$\lambda_{em}$ 665 nm, and standardization at $\lambda_{em}$ 620 nm) by means of a PHERASTAR reader (BMG).

The result is calculated using the following formula:

Delta_F=100×[ratio(100%)−ratio(background)]/ratio (background)

in which "ratio(100%)" represents the ratio of fluorescence $\lambda_{em}$665/$\lambda_{em}$620, of the fluorescent antibodies in the presence of SASPase$_{SEQ\ ID\ NO:\ 8}$-GST and FLG2$_{SEQ\ ID\ NO:\ 4}$-His-THX, and "ratio(background)" represents the ratio of fluorescence $\lambda_{em}$665/$\lambda_{em}$620, of the fluorescent antibodies in the absence of the peptides.

Delta_F is determined in the presence "Delta_F Assay", or in the absence "Delta_F Control", of the compounds tested (control in DMSO).

The "final ratio" reflecting the percentage inhibition or percentage activation of the interaction of the peptides is then calculated using the following formula:

Final ratio=100×(Delta_F Assay−Delta_F Control)/ (Delta_F Control)

A decrease in this final ratio indicates the presence of compounds capable of preventing or destabilizing the SASPase$_{SEQ\ ID\ NO:\ 16}$-GST/FLG2$_{SEQ\ ID\ NO:\ 9}$-His-THX interaction.

An increase in this final ratio indicates the presence of compounds capable of stabilizing or promoting this interaction.

The screening protocol of the invention proves to be particularly advantageous for identifying active compounds capable of positively or negatively modulating the interaction between a peptide from FLG2 and SASPase or a peptide from SASPase.

These screened active compounds are capable of being advantageously used with regard to esthetic or pathological disorders of the skin and/or its appendages resulting from a defect in the proliferation and/or differentiation of the cells of the epidermis.

---

The invention claimed is:

1. A chimeric peptide comprising a first amino acid sequence from filaggrin-2 fused to a second amino acid sequence,
wherein the first amino acid sequence represents a peptide represented by the amino acid sequence selected from the group consisting of SEQ ID NO: 9, SEQ ID NO: 10, SEQ ID NO: 11, SEQ ID NO: 12, SEQ ID NO: 13, SEQ ID NO: 14, and SEQ ID NO: 15, and a homolog having a sequence identity of at least 85% to SEQ ID NO: 10, SEQ ID NO: 11, SEQ ID NO: 12, SEQ ID NO: 13, SEQ ID NO: 14 and SEQ ID NO: 15 and modifies the three-dimensional conformation of a complex formed by interaction of filaggrin-2 with skin aspartic protease.

2. The chimeric peptide as claimed in claim 1, wherein the second amino acid sequence is selected from the group consisting of a fluorescent protein, an affinity label, a signal peptide and a propenetrating peptide.

3. An isolated complex formed by interaction of a first amino acid sequence from filaggrin-2 with a second amino acid sequence from skin aspartic protease, or a homolog thereof having a sequence identity of at least 85%,
wherein the first amino acid sequence represents a peptide represented by the amino acid sequence selected from the group consisting of SEQ ID NO: 9, SEQ ID NO: 10, SEQ ID NO: 11, SEQ ID NO: 12, SEQ ID NO: 13, SEQ ID NO: 14, and SEQ ID NO: 15, and a homolog having a sequence identity of at least 85% to SEQ ID NO: 10, SEQ ID NO: 11, SEQ ID NO: 12, SEQ ID NO: 13, SEQ ID NO: 14 and SEQ ID NO: 15 and modifies the three-dimensional conformation of a complex formed by interaction of the first amino acid sequence with the second amino acid sequence.

* * * * *

SEQUENCE LISTING

<160> NUMBER OF SEQ ID NOS: 16

<210> SEQ ID NO 1
<211> LENGTH: 285
<212> TYPE: DNA
<213> ORGANISM: Homo sapiens
<220> FEATURE:
<221> NAME/KEY: source
<222> LOCATION: 1..285
<223> OTHER INFORMATION: /mol_type="DNA"
      /organism="Homo sapiens"

<400> SEQUENCE: 1
accgacctct tgagaagtgt tgtcaccgta attgatgttt tctacaaata caccaagcaa      60
gatggggagt gtggcacact gagcaagggt gaactaaagg aacttctgga gaaagagctt     120
catccagttc tgaagaaccc agatgatcca gacacagtgg atgtcatcat gcatatgctg     180
gatcgagatc atgacagaag attggacttt actgagtttc ttttgatgat attcaagctg     240
actatggcct gcaacaaggt cctcagcaaa gaatactgca aagct                     285

<210> SEQ ID NO 2
<211> LENGTH: 60
<212> TYPE: DNA
<213> ORGANISM: Homo sapiens
<220> FEATURE:
<221> NAME/KEY: source
<222> LOCATION: 1..60
<223> OTHER INFORMATION: /mol_type="DNA"
      /organism="Homo sapiens"

<400> SEQUENCE: 2
tttactgagt ttcttttgat gatattcaag ctgactatgg cctgcaacaa ggtcctcagc      60

<210> SEQ ID NO 3
<211> LENGTH: 45
<212> TYPE: DNA
<213> ORGANISM: Homo sapiens
<220> FEATURE:
<221> NAME/KEY: source
<222> LOCATION: 1..45

```
<223> OTHER INFORMATION: /mol_type="DNA"
        /organism="Homo sapiens"

<400> SEQUENCE: 3
gagtttcttt tgatgatatt caagctgact atggcctgca acaag            45

<210> SEQ ID NO 4
<211> LENGTH: 45
<212> TYPE: DNA
<213> ORGANISM: Homo sapiens
<220> FEATURE:
<221> NAME/KEY: source
<222> LOCATION: 1..45
<223> OTHER INFORMATION: /mol_type="DNA"
        /organism="Homo sapiens"

<400> SEQUENCE: 4
ctcatgatat tcaagctgac tatggcctgc aacaaggtcc tcagc            45

<210> SEQ ID NO 5
<211> LENGTH: 39
<212> TYPE: DNA
<213> ORGANISM: Homo sapiens
<220> FEATURE:
<221> NAME/KEY: source
<222> LOCATION: 1..39
<223> OTHER INFORMATION: /mol_type="DNA"
        /organism="Homo sapiens"

<400> SEQUENCE: 5
ctcatgatat tcaagctgac tatggcctgc aacaaggtc                   39

<210> SEQ ID NO 6
<211> LENGTH: 48
<212> TYPE: DNA
<213> ORGANISM: Homo sapiens
<220> FEATURE:
<221> NAME/KEY: source
<222> LOCATION: 1..48
<223> OTHER INFORMATION: /mol_type="DNA"
        /organism="Homo sapiens"

<400> SEQUENCE: 6
actgagtttc ttttgatgat attcaagctg actatggcct gcaacaag         48

<210> SEQ ID NO 7
<211> LENGTH: 24
<212> TYPE: DNA
<213> ORGANISM: Homo sapiens
<220> FEATURE:
<221> NAME/KEY: source
<222> LOCATION: 1..24
<223> OTHER INFORMATION: /mol_type="DNA"
        /organism="Homo sapiens"

<400> SEQUENCE: 7
actgagtttc ttttgatgat attc                                   24

<210> SEQ ID NO 8
<211> LENGTH: 231
<212> TYPE: DNA
<213> ORGANISM: Homo sapiens
<220> FEATURE:
<221> NAME/KEY: source
<222> LOCATION: 1..231
<223> OTHER INFORMATION: /mol_type="DNA"
        /organism="Homo sapiens"

<400> SEQUENCE: 8
```

```
cggcagcatg ccttcgtccc ggaacctttt gatggggcca atgtcgtccc aaacctctgg      60
ctgcacagct ttgaagtcat caatgacctc aaccattggg accatatcac caagctaagg     120
ttcctgaaag agtccctcag aggagaggcc ctgggtgtct acaataggct cagtccccag     180
gaccagggag actatgggac tgtgaaagag gccctcctga aggcctttgg g              231
```

```
<210> SEQ ID NO 9
<211> LENGTH: 95
<212> TYPE: PRT
<213> ORGANISM: Homo sapiens
<220> FEATURE:
<221> NAME/KEY: SOURCE
<222> LOCATION: 1..95
<223> OTHER INFORMATION: /mol_type="protein"
      /organism="Homo sapiens"

<400> SEQUENCE: 9
```

Thr Asp Leu Leu Arg Ser Val Val Thr Val Ile Asp Val Phe Tyr Lys
1               5                   10                  15

Tyr Thr Lys Gln Asp Gly Glu Cys Gly Thr Leu Ser Lys Gly Glu Leu
            20                  25                  30

Lys Glu Leu Leu Glu Lys Glu Leu His Pro Val Leu Lys Asn Pro Asp
        35                  40                  45

Asp Pro Asp Thr Val Asp Val Ile Met His Met Leu Asp Arg Asp His
    50                  55                  60

Asp Arg Arg Leu Asp Phe Thr Glu Phe Leu Leu Met Ile Phe Lys Leu
65                  70                  75                  80

Thr Met Ala Cys Asn Lys Val Leu Ser Lys Glu Tyr Cys Lys Ala
                85                  90                  95

```
<210> SEQ ID NO 10
<211> LENGTH: 20
<212> TYPE: PRT
<213> ORGANISM: Homo sapiens
<220> FEATURE:
<221> NAME/KEY: SOURCE
<222> LOCATION: 1..20
<223> OTHER INFORMATION: /mol_type="protein"
      /organism="Homo sapiens"

<400> SEQUENCE: 10
```

Phe Thr Glu Phe Leu Leu Met Ile Phe Lys Leu Thr Met Ala Cys Asn
1               5                   10                  15

Lys Val Leu Ser
            20

```
<210> SEQ ID NO 11
<211> LENGTH: 15
<212> TYPE: PRT
<213> ORGANISM: Homo sapiens
<220> FEATURE:
<221> NAME/KEY: SOURCE
<222> LOCATION: 1..15
<223> OTHER INFORMATION: /mol_type="protein"
      /organism="Homo sapiens"

<400> SEQUENCE: 11
```

Glu Phe Leu Leu Met Ile Phe Lys Leu Thr Met Ala Cys Asn Lys
1               5                   10                  15

```
<210> SEQ ID NO 12
<211> LENGTH: 15
<212> TYPE: PRT
```

```
<213> ORGANISM: Homo sapiens
<220> FEATURE:
<221> NAME/KEY: SOURCE
<222> LOCATION: 1..15
<223> OTHER INFORMATION: /mol_type="protein"
      /organism="Homo sapiens"

<400> SEQUENCE: 12

Leu Met Ile Phe Lys Leu Thr Met Ala Cys Asn Lys Val Leu Ser
1               5                   10                  15

<210> SEQ ID NO 13
<211> LENGTH: 13
<212> TYPE: PRT
<213> ORGANISM: Homo sapiens
<220> FEATURE:
<221> NAME/KEY: SOURCE
<222> LOCATION: 1..13
<223> OTHER INFORMATION: /mol_type="protein"
      /organism="Homo sapiens"

<400> SEQUENCE: 13

Leu Met Ile Phe Lys Leu Thr Met Ala Cys Asn Lys Val
1               5                   10

<210> SEQ ID NO 14
<211> LENGTH: 16
<212> TYPE: PRT
<213> ORGANISM: Homo sapiens
<220> FEATURE:
<221> NAME/KEY: SOURCE
<222> LOCATION: 1..16
<223> OTHER INFORMATION: /mol_type="protein"
      /organism="Homo sapiens"

<400> SEQUENCE: 14

Thr Glu Phe Leu Leu Met Ile Phe Lys Leu Thr Met Ala Cys Asn Lys
1               5                   10                  15

<210> SEQ ID NO 15
<211> LENGTH: 8
<212> TYPE: PRT
<213> ORGANISM: Homo sapiens
<220> FEATURE:
<221> NAME/KEY: SOURCE
<222> LOCATION: 1..8
<223> OTHER INFORMATION: /mol_type="protein"
      /organism="Homo sapiens"

<400> SEQUENCE: 15

Thr Glu Phe Leu Leu Met Ile Phe
1               5

<210> SEQ ID NO 16
<211> LENGTH: 77
<212> TYPE: PRT
<213> ORGANISM: Homo sapiens
<220> FEATURE:
<221> NAME/KEY: SOURCE
<222> LOCATION: 1..77
<223> OTHER INFORMATION: /mol_type="protein"
      /organism="Homo sapiens"

<400> SEQUENCE: 16

Arg Gln His Ala Phe Val Pro Glu Pro Phe Asp Gly Ala Asn Val Val
1               5                   10                  15

Pro Asn Leu Trp Leu His Ser Phe Glu Val Ile Asn Asp Leu Asn His
            20                  25                  30
```

-continued

```
Trp Asp His Ile Thr Lys Leu Arg Phe Leu Lys Glu Ser Leu Arg Gly
            35                  40                  45

Glu Ala Leu Gly Val Tyr Asn Arg Leu Ser Pro Gln Asp Gln Gly Asp
        50                  55                  60

Tyr Gly Thr Val Lys Glu Ala Leu Leu Lys Ala Phe Gly
65                  70                  75
```